(12) United States Patent  
Stansfield et al.

(10) Patent No.: US 7,767,660 B2
(45) Date of Patent: Aug. 3, 2010

(54) ANTIVIRAL INDOLES

(75) Inventors: Ian Stansfield, Rome (IT); Uwe Koch, Rome (IT); Joerg Habermann, Rome (IT); Frank Narjes, Rome (IT)

(73) Assignee: Istituto di Richerche di Biologia Molecolare P. Angeletti SpA, Pomezia, Rome (IT)

( * ) Notice: Subject to any disclaimer, the term of this patent is extended or adjusted under 35 U.S.C. 154(b) by 273 days.

(21) Appl. No.: 12/002,996

(22) Filed: Dec. 19, 2007

(65) Prior Publication Data

US 2008/0214522 A1 Sep. 4, 2008

(51) Int. Cl.
*C07D 267/22* (2006.01)
*A61K 31/55* (2006.01)

(52) U.S. Cl. ............. 514/183; 514/211.09; 514/214.02; 514/219; 540/457

(58) Field of Classification Search ................. 540/457; 514/183, 211.09, 214.02, 219
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,608,027 B1 | 8/2003 | Tsantrizos et al. | |
| 6,777,395 B2 | 8/2004 | Bhat et al. | |
| 6,955,174 B2 | 10/2005 | Friedrichs et al. | |
| 7,470,664 B2 | 12/2008 | Holloway et al. | |
| 2002/0019363 A1 | 2/2002 | Ismaili et al. | |
| 2002/0107138 A1 | 8/2002 | Hoveyda et al. | |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |
| 2004/0229776 A1 | 11/2004 | Chen et al. | |
| 2004/0229818 A1 | 11/2004 | Llinas-Brunet et al. | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2006/0257980 A1 | 11/2006 | Li | |
| 2007/0027071 A1 | 2/2007 | Holloway et al. | |

FOREIGN PATENT DOCUMENTS

| | | |
|---|---|---|
| EP | 1 719 773 A1 | 11/2006 |
| EP | 1719773 A1 | 11/2006 |
| GB | 2337262 A | 11/1999 |
| GB | 2430621 A | 4/2007 |
| WO | WO 93/00334 A1 | 1/1993 |
| WO | WO 96/37619 A1 | 11/1996 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | WO 02/59321 A2 | 8/2002 |
| WO | 02/100415 A2 | 12/2002 |

(Continued)

OTHER PUBLICATIONS

V. Lohman et al., 285 Science 110-13 (1999).

(Continued)

*Primary Examiner*—Bruck Kifle
(74) *Attorney, Agent, or Firm*—Julie M. Lake; Sheldon O. Heber

(57) ABSTRACT

Compounds of the formula (I):

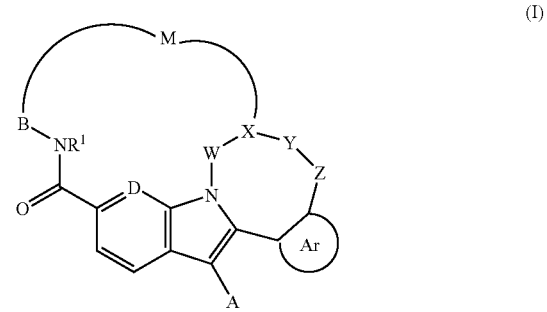

wherein A, B, D, M, Ar, W, X, Y, Z and $R^1$ are as defined herein, are useful in the prevention and treatment of hepatitis C infections. The compounds, their preparation, pharmaceutical compositions containing them and their use in medicine are disclosed.

15 Claims, No Drawings

FOREIGN PATENT DOCUMENTS

| | | |
|---|---|---|
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | WO 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | WO 2005/080399 A1 | 9/2005 |
| WO | 2006/008556 A1 | 1/2006 |
| WO | 2006/020082 A1 | 2/2006 |
| WO | WO 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | WO 2006/029912 A1 | 3/2006 |
| WO | 2006/046030 A1 | 5/2006 |
| WO | 2006/046039 A2 | 5/2006 |
| WO | WO 2006/046030 A2 | 5/2006 |
| WO | WO 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Volker Lohmann et al., 274(16) The Journal of Biological Chemistry 10807-15 (1999).

W. Clark Still et al., 43(14) Journal of Organic Chemistry 2923-25 (1978).

J.M. Travins & F.A. Etzkorn, 39 Tetrahedron Letters 9389-92 (1998).

Brian W. Dymock et al., "Novel Approaches to the Treatment of Hepatitis C Virus Infection," 11 Antiviral Chemistry & Chemotherapy 79-96 (2000).

Hugo R. Rosen & David R. Gretch, "Hepatitis C virus: current understanding and prospects for future therapies," 5 Molec. Med. Today 393-99 (1999).

Darius Moradpour & Hubert E. Blum, "Current and evolving therapies for hepatitis C," 11 Euro. J. Gastroenterol. Hepatol. 1189-1202 (1999).

Ralf Bartenschlager, "Candidate Targets for Hepatitis C Virus-Specific Antiviral Therapy," 40(5-6) Intervirology 378-93 (1997).

Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).

Brain W. Dymock, "Emerging therapies for hepatitis C virus infection," 6 Emerging Drugs 13-42 (2001).

Charlene Crabb, Infectious Diseases. "Hard-Won Advances Spark Excitement about Hepatitis C," Science 506-507 (2001).

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

Alois Furstner et al., "Total Synthesis and Structural Refinement of the Cyclic Tripyrrole Pigment Nonylprodigiosin," 64 J. Org. Chem. 8275-80 (1999).

Tina M. Trnka & Robert H. Grubbs, "The Development of L2X2R-CHR Olefin Metathesis Catalysts: An Organometallic Success Story," 34 Acc. Chem. Res. 18-29 (2001).

A. Srikrishna et al., "Enantiospecific Construction of the BC-ring System of Taxanes," 45 Tetrahedron Letters 2939-42 (2004).

Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

Eusebio Juaristi & Hugo A. Jimenez-Vazquez, "Single Electron Transfer Mechanism in the Reaction of 1,3-Dithanyllithium and Alkyl Iodides," 56 J. Org. Chem. 1623-30 (1991).

Paola Conti et al., "Chemoenzymatic Synthesis of the Enantiomers of Desoxymuscarine," 9 Tetrahedron: Asymmetry 657-65 (1998).

Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).

D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., "Molecular Modeling Based Approach to Potent P2-P4 Macrocyclic Inhibitors of Hepatitis C NS3/NS4A Protease," 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl) boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

Youwei Yan et al., Complex of NS3 protease and NS4A peptide of BK strain hepatitis C virus: A 2.2 Angstrom resolution structure in a hexagonal crystal form, 7 Protein Science 837 (1998).

ANTIVIRAL INDOLES

CROSS-REFERENCE TO RELATED APPLICATIONS

This application claims priority to British Provisional application GB 0625345.4, filed Dec. 20, 2006, which is incorporated herein by reference in its entirety.

FIELD OF THE INVENTION

The present invention relates to macrocyclic indole compounds, to pharmaceutical compositions containing them, to their use in the prevention and treatment of hepatitis C infections and to methods of preparation of such compounds and compositions.

BACKGROUND OF THE INVENTION

Hepatitis C (HCV) is a cause of viral infections. There is as yet no adequate treatment for HCV infection but it is believed that inhibition of its RNA polymerase in mammals, particularly humans, would be of benefit.

Published International patent application WO 93/00334 (Fidia-Georgetown Institute for the Neurosciences) discloses the following indole derivatives:

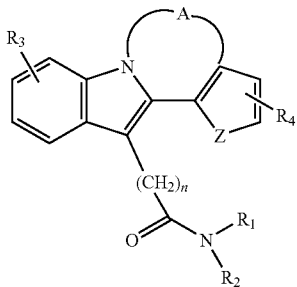

where A, Z, $R_1$, $R_2$, $R_3$, $R_4$ and n are defined therein, as useful in compositions and methods for treating psychiatric and neurological disorders. However, this document does not disclose the use of tetracyclic indole derivatives in treating or preventing viral infections.

Published International patent application WO 2005/080399 (Japan Tobacco Inc.) discloses the following fused heterotetracyclic compounds:

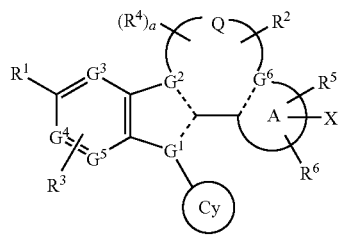

where A, X, Cy, $G^1$, $G^2$, $G^3$, $G^4$, $G^5$, $G^6$, $R^1$, $R^2$, $R^3$, $R^4$, $R^5$, $R^6$ and a are defined therein, and their use as HCV polymerase inhibitors.

Published International patent application WO 2006/020082 (Bristol-Myers Squibb Company) discloses the following fused tetracyclic compounds:

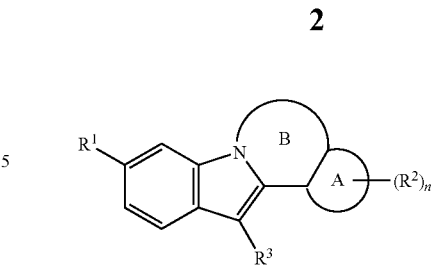

where A, B, $R^1$, $R^2$, $R^3$ and n are defined therein, and their use in treating hepatitis C.

Published International applications WO2006/046030 and WO2006/046039 (both Istituto Di Ricerche Di Biologia Molecolare P. Angeletti SpA) disclose certain tetracyclic indole derivatives:

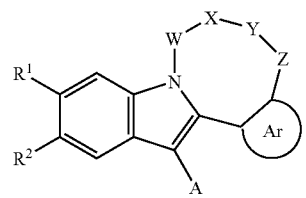

wherein $R^1$, $R^2$, A, Ar, W, X, Y, and Z are defined therein, useful for the treatment or prevention of infection by hepatitis C virus.

SUMMARY OF THE INVENTION

Thus, the present invention provides the compound of the formula (I):

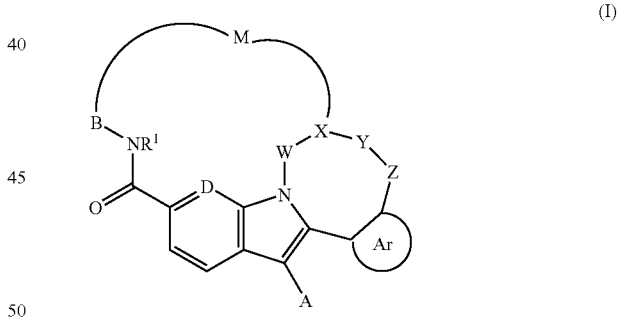

(I)

wherein

Ar is a moiety containing at least one aromatic ring and possesses 5-, 6-, 9- or 10-ring atoms optionally containing 1, 2 or 3 heteroatoms independently selected from N, O and S, which ring is optionally substituted by groups $Q^1$ and $Q^2$;

$Q^1$ is halogen, hydroxy, $C_{1-6}$alkyl, $C_{1-6}$alkoxy, aryl, heteroaryl, $CONR^aR^b$, $(CH_2)_{0-3}NR^aR^b$, $O(CH_2)_{1-3}NR^aR^b$, $O(CH_2)_{0-3}CONR^aR^b$, $O(CH_2)_{0-3}$aryl, $O(CH_2)_{0-3}$heteroaryl, $O(CR^eR^f)$aryl, $O(CR^eR^f)$heteroaryl or $OCHR^cR^d$;

$R^a$ and $R^b$ are each independently selected from hydrogen, $C_{1-4}$alkyl and $C(O)C_{1-4}$alkyl;

or $R^a$, $R^b$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

$R^c$ and $R^d$ are each independently selected from hydrogen and $C_{1-4}$alkoxy;

or $R^c$ and $R^d$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$R^e$ is hydrogen or $C_{1-6}$alkyl;

$R^f$ is $C_{1-6}$alkyl;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;

A is $C_{3-6}$alkyl or $C_{2-6}$alkenyl, or A is a non-aromatic ring of 3 to 8 ring atoms where said ring may contain a double bond and/or may contain a O, S, SO, $SO_2$ or NH moiety, or A is a non-aromatic bicyclic moiety of 4 to 8 ring atoms, and A is optionally substituted by halogen, hydroxy, $C_{1-4}$alkyl or $C_{1-4}$alkoxy;

D is N or $CR^g$;

$R^g$ is hydrogen, fluorine, chlorine, $C_{1-4}$alkyl, $C_{2-4}$alkenyl or $C_{1-4}$alkoxy, where said $C_{1-4}$alkyl, $C_{2-4}$alkenyl and $C_{1-4}$alkoxy groups are optionally substituted by hydroxy or fluorine;

W is a bond, C=O, O, $S(O)_{0-2}$ or —$(CR^{10}R^{11})$—$(CR^{12}R^{13})_{0-1}$—;

Y is a bond, C=O, O, —$CR^{14}R^{15}$— or $NR^{14}$;

Z is a bond, C=O, O, $S(O)_{0-2}$, —$(CR^{10}R^{11})$—$(CR^{12}R^{13})_{0-1}$— or $NR^{10}$;

and none, one or two of W, Y and Z are a bond;

X is —$CR^{14a}$— or N;

$R^{10}$, $R^{11}$, $R^{12}$, $R^{13}$, $R^{14}$, $R^{14a}$ and $R^{15}$ are each independently selected from hydrogen, hydroxy, $C_{1-6}$alkyl, $C_{2-6}$alkenyl, $C_{1-6}$alkoxy, $C(O)C_{1-6}$alkyl, Het, $(CH_2)_{0-3}NR^{16}R^{17}$, $C(O)(CH_2)_{0-3}NR^{16}R^{17}$, $NHC(O)(CH_2)_{0-3}NR^{16}R^{17}$, O$(CH_2)_{1-3}$ $NR^{16}R^{17}$, $S(O)_{0-2}(CH_2)_{0-3}R^{16}R^{17}$ and $C(O)(CH_2)_{0-3}$ $OR^{16}$;

or one of $R^{10}$, $R^{14}$ and $R^{14a}$ is linked to $R^{22}$ or $R^{23}$ to form a ring of 4 to 10 atoms, where said ring is optionally substituted by halogen, hydroxy, $C_{1-4}$alkyl or $C_{1-4}$alkoxy; Het is a heteroaliphatic ring of 4 to 7 ring atoms, which ring may contain 1, 2 or 3 heteroatoms selected from N, O or S or a group S(O), $S(O)_2$, NH or $NC_{1-4}$alkyl;

$R^{16}$ and $R^{17}$ are independently selected from hydrogen, $C_{1-6}$alkyl and $(CH_2)_{0-4}NR^{18}R^{19}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

$R^{18}$ and $R^{19}$ are independently selected from hydrogen and $C_{1-6}$alkyl;

or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

$R^1$ is hydrogen or $C_{1-6}$alkyl;

B is —$CR^{20}R^{21}$—, —C(=O)—, —SO— or —$SO_2$—;

$R^{20}$ and $R^{21}$ are independently selected from hydrogen and $C_{1-6}$alkyl;

or $R^{20}$ and $R^{21}$, together with the carbon atom to which they are joined, form a $C_{3-6}$cycloalkyl group;

M is $C_{4-8}$alkylene or $C_{4-8}$alkenylene, optionally substituted by $R^{22}$, where 1, 2 or 3 of the carbon atoms in the $C_{4-8}$alkylene or $C_{4-8}$alkenylene groups is optionally replaced by O, $NR^{23}$, S, SO, $SO_2$, piperidinyl, piperazinyl or pyrrolidinyl, where $R^{23}$ is hydrogen or $C_{1-6}$alkyl, or $R^{23}$ is linked to one of $R^{10}$, $R^{14}$ and $R^{14a}$ to form a ring of 4 to 10 atoms as hereinbefore described;

where $R^{22}$ is halo, $C_{1-4}$alkyl, $(CH_2)_{0-3}C_{3-8}$cycloalkyl, $(CH_2)_{0-3}$ aryl, $(CH_2)_{0-3}$heteroaryl, $(CH_2)_{0-3}$Het or oxo, or $R^{22}$ is linked to one of $R^{10}$, $R^{14}$ and $R^{14a}$ to form a ring of 4 to 10 atoms as hereinbefore described;

and pharmaceutically acceptable salts thereof.

DETAILED DESCRIPTION OF THE INVENTION

In one embodiment of the present invention, Ar is a five- or six-membered aromatic ring optionally containing 1, 2 or 3 heteroatoms independently selected from N, O and S, and which ring is optionally substituted by groups $Q^1$ and $Q^2$ as hereinbefore defined.

Preferably, Ar is a five- or six-membered aromatic ring optionally containing 1 or 2 heteroatoms independently selected from N, O or S, such as phenyl, pyridyl, pyridazinyl, pyrimidinyl, pyrazinyl, furanyl, pyrazolyl, imidazolyl and thienyl, which ring is optionally substituted by groups $Q^1$ and $Q^2$ as hereinbefore defined. More preferably, Ar is phenyl, 2-pyridyl, 3-pyridyl, 4-pyridyl, 2-furanyl or 3-furanyl, particularly phenyl, optionally substituted by groups $Q^1$ and $Q^2$ as hereinbefore defined.

Preferably, $Q^1$ is halogen, hydroxy, $C_{1-4}$alkyl or $C_{1-4}$alkoxy. More preferably, $Q^1$ is fluorine, chlorine, methyl or methoxy. Most preferably, $Q^1$ is methoxy.

Preferably, $Q^2$ is absent.

In a further embodiment, A is $C_{3-6}$alkyl, $C_{2-6}$alkenyl or $C_{3-8}$cycloalkyl, where A is optionally substituted by halogen, hydroxy, $C_{1-4}$alkyl or $C_{1-4}$alkoxy. Preferably, A is $C_{3-8}$cycloalkyl, more preferably cyclopentyl or cyclohexyl, most preferably cyclohexyl, optionally substituted by halogen, hydroxy, $C_{1-4}$alkyl or $C_{1-4}$alkoxy.

Preferably, A is unsubstituted or substituted by fluorine, chlorine, methyl or methoxy, particularly fluorine. More preferably, A is unsubstituted or substituted by fluorine. Examples of suitable A groups include cyclohexyl and fluorocyclohexyl, especially 2-fluorocyclohexyl.

In a further embodiment, D is $CR^g$ where $R^g$ is as hereinbefore defined. Preferably, $R^g$ is hydrogen or $C_{1-4}$alkyl. More preferably, $R^g$ is hydrogen.

In a further embodiment, W is a bond, C=O or —$(CR^{10}R^{11})$—$(CR^{12}R^{13})_{0-1}$— where $R^{10}$, $R^{11}$, $R^{12}$ and $R^{13}$ are as hereinbefore defined. Preferably, W is —$(CR^{10}R^{11})$—$(CR^{12}R^{13})_{0-1}$—. More preferably, W is —$CH_2$— or —$CH_2CH_2$—. Most preferably, W is —$CH_2$—.

In a further embodiment, Z is a bond, C=O, O, —$(CR^{10}R^{11})$—$(CR^{12}R^{13})_{0-1}$— or $NR^{10}$ where $R^{10}$, $R^{11}$, $R^{12}$ and $R^{13}$ are as hereinbefore defined. Preferably, Z is a bond, O or —$(CR^{10}R^{11})$—$(CR^{12}R^{13})_{0-1}$—. More preferably, Z is a bond, O, —$CH_2$— or —$CH_2CH_2$—. Most preferably, Z is O.

In a further embodiment, Y is C=O, O, —$CR^{14}R^{15}$— or $NR^{14}$ where $R^{14}$ and $R^{15}$ are as hereinbefore defined. Preferably, Y is O, —$CR^{14}R^{15}$— or $NR^{14}$. More preferably, Y is —CH$_2$—, NH, N(C$_{1-6}$alkyl), NCH$_2$CH$_2$N(C$_{1-6}$alkyl)$_2$ or NC(O)(CH$_2$)$_{1-2}$N(C$_{1-6}$alkyl)$_2$. Most preferably, Y is —CH$_2$—, NH, N(C$_{1-4}$alkyl), N(CH$_2$)$_2$N(C$_{1-4}$alkyl)$_2$ or NC(O)CH$_2$N(C$_{1-4}$alkyl)$_2$. Especially, Y is —CH$_2$—, NCH$_3$ or N(CH$_2$)$_2$N(CH$_3$)$_2$. More especially, Y is —CH$_2$—.

In a further embodiment, X is —CR$^{14}$—, where R$^{14}$ is as hereinbefore defined. Preferably, X is —CH— or —C(C$_{1-6}$alkyl)-. More preferably, X is —CH—.

In a further embodiment, R$^1$ is hydrogen or methyl. Preferably, R$^1$ is hydrogen.

In a further embodiment, B is —CH$_2$— or —SO$_2$—. Preferably, B is —SO$_2$—.

In a further embodiment, M is C$_{4-8}$alkylene, optionally substituted by halo, C$_{1-4}$alkyl or oxo, where 1 or 2 of the carbon atoms in the C$_{4-8}$alkylene group is optionally replaced by O, NR$^{23}$, S, SO or SO$_2$, where R$^{23}$ is as hereinbefore defined. Preferably, M is C$_{5-8}$alkylene, optionally substituted by C$_{1-4}$alkyl or oxo, where 1 or 2 of the carbon atoms in the C$_{5-8}$alkylene group is replaced by O, NH or N(C$_{1-4}$alkyl). Examples of suitable M groups include:

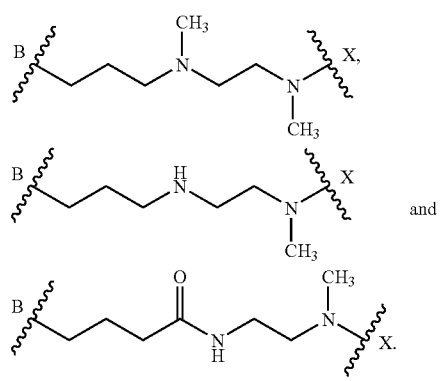

In one embodiment of the present invention, there is provided the compound of formula (Ia):

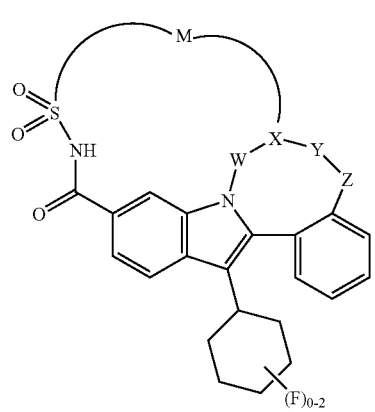

(Ia)

or a pharmaceutically acceptable salt thereof, wherein W, X, Y, Z and M are as defined in relation to formula (I).

When any variable occurs more than one time in formula (I) or in any substituent, its definition on each occurrence is independent of its definition at every other occurrence.

As used herein, the term "alkyl" or "alkoxy" as a group or part of a group means that the group is straight or branched.

Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl.

As used herein, the term "alkenyl" and "alkynyl" as a group or part of a group means that the group is straight or branched. Examples of suitable alkenyl groups include vinyl and allyl. A suitable alkynyl group is propargyl.

As used herein, the term "alkylene" means that the alkyl group links two separate groups and may be straight or branched. Examples of suitable alkylene groups include ethylene [—CH$_2$—CH$_2$—] and propylene [—CH$_2$—CH$_2$—CH$_2$—, —CH(CH$_3$)—CH$_2$— or —CH$_2$—CH(CH$_3$)—]. The terms "alkenylene" and "alkynylene" shall be construed in an analogous manner.

When used herein, the term "halogen" means fluorine, chlorine, bromine and iodine.

When used herein, the term "aryl" as a group or part of a group means a carbocyclic aromatic ring. Examples of suitable aryl groups include phenyl and naphthyl.

When used herein, the term "heteroaryl" as a group or part of a group means a 5- to 10-membered heteroaromatic ring system containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl, benzofuryl, quinolinyl and isoquinolinyl.

Where a compound or group is described as "optionally substituted" one or more substituents may be present. Furthermore, optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include:
45 101: (7R)-14-cyclohexyl-21,24-dimethyl-7,8-dihydro-6H-7,11-(epiminoethanoiminopropanothio iminomethano)indolo[1,2-e][1,5]benzoxazocin-15-one 17,17-dioxide,
102: (7R)-14-cyclohexyl-24-methyl-7,8-dihydro-6H-7,11-(epiminoethanoiminopropanothioimino methano)indolo[1,2-e][1,5]benzoxazocin-15-one 17,17-dioxide,
201: (7R)-14-cyclohexyl-25-methyl-7,8-dihydro-6H-7,11-(epiminoethanoiminobutanothioimino methano)indolo[1,2-e][1,5]benzoxazocine-15,21-dione 17,17-dioxide,
301: (7R)-14-[(1R,2S) or (1S,2R)-2-fluorocyclohexyl]-21,24-dimethyl-7,8-dihydro-6H-7,11-(epiminoethanoiminopropanothioiminomethano)indolo[1,2-e][1,5]benzoxazocin-15-one 17,17-dioxide, and pharmaceutically acceptable salts thereof.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope any enantiomers, diastereomers, geometric isomers and tautomers of the compounds of formula (I). It is to be understood that all such isomers and mixtures thereof are encompassed within the scope of the invention.

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

In a further aspect, the invention provides a method of inhibiting hepatitis C virus polymerase and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 1 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

The present invention also provides a process for the preparation of compounds of formula (I).

According to a general process (a), compounds of formula (I) may be prepared by internal ring closure of the compound of formula (II):

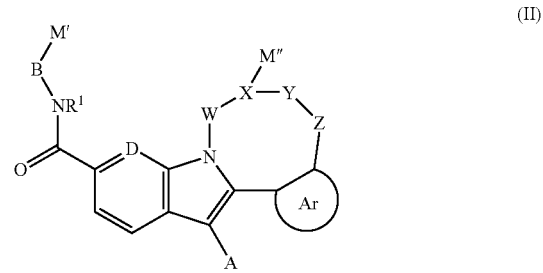

where A, Ar, B, D, R¹, W, X, Y and Z are as defined in relation to formula (I), and M' and M" have suitable precursor functionality to form group M as defined in relation to formula (I). For instance, when M is —CH₂—CH₂—CH₂—NH—CH₂—CH₂—N(CH₃)—, M' can be —CH₂—CH₂—CH₂Cl and M" can be —N(CH₃)—CH₂—CH₂—NH₂, where the reaction is carried out in the presence of a mild base, such as diisopropylethylamine, in a suitable solvent, such as acetonitrile or DMF, under microwave irradiation. Alternatively, when M is —CH₂—CH₂—CH₂—C(=O)—NH—CH₂—CH₂—N (CH$_3$)—, M' can be —CH$_2$—CH$_2$—CH$_2$—CO$_2$H and M" can be —N(CH$_3$)—CH$_2$—CH$_2$—NH$_2$, where the reaction is carried out in the presence of a coupling reagent, such as HATU, and a base, such as diisopropylethylamine, in a suitable solvent, such as DMF.

Compounds of formula (II) are either known in the art or may be prepared by conventional methodology well known to one of ordinary skill in the art using, for instance, procedures described in the accompanying Descriptions and Examples, or by alternative procedures which will be readily apparent.

Compounds of formula (I) can be converted into other compounds of formula (I) using synthetic methodology well known in the art. For instance, the compound of formula (I) where M comprises an N—H group may be converted into the compound of formula (I) where M comprises an N—CH$_3$ group by methylation using formaldehyde followed by a mild reducing agent, such as sodium borohydride.

General Synthetic Schemes

Two general strategies were employed for assembly of compounds from the macrocyclic class (Methods A and B); Method B can be regarded as an extension of Method A.

A suitably functionalised tether was assembled first (as described in published International applications WO 2006/046030 and WO 2006/046039). A precursor fragment to one section of the macrocycle was installed on the tether, with subsequent unmasking of the acid at C6 and functionalisation to introduce a precursor fragment to the remaining segment of the macrocycle. Functional group manipulation and macrocyclisation (e.g., via amide bond formation, alkylation, reductive amination, metathesis etc.) set up the macrocycle. Potentially, the bond formed in ring closure could be at almost any point around the macrocyclic linker (e.g., forming the acylsulfonamide bond could also be the ring closing step).

Method A

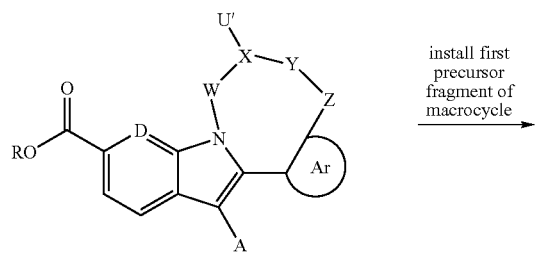

install first precursor fragment of macrocycle

Method B

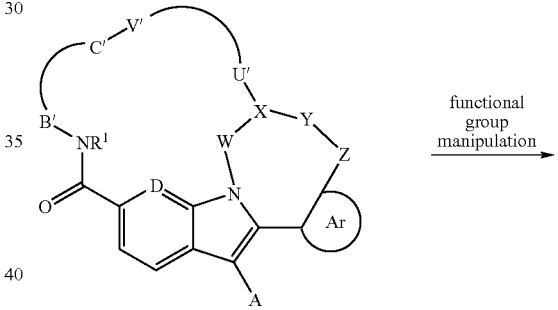

functional group manipulation

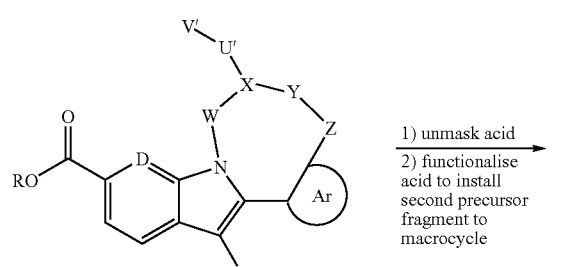

1) unmask acid
2) functionalise acid to install second precursor fragment to macrocycle

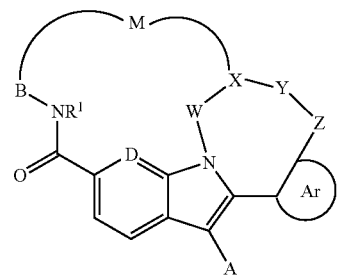

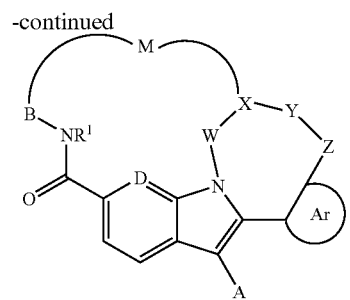

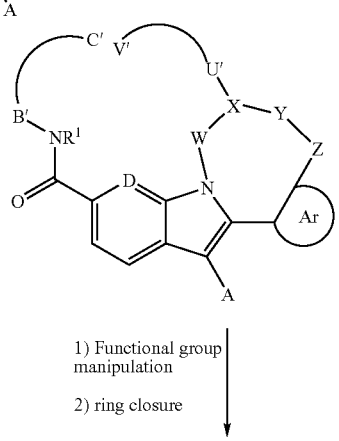

1) Functional group manipulation
2) ring closure

Functional groups on the macrocycle were manipulated post-closure, e.g., via reductive amination, alkylation, amide reduction, amide formation etc. Potentially, sidechains can branch from any point around the macrocyclic linker.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The present invention is illustrated further by the following non-limiting examples.

The compounds of the invention were tested for inhibitory activity against the HCV RNA dependent RNA polymerase (NS5B) in an enzyme inhibition assay (example i)) and in a cell based sub-genomic replication assay (example ii)). The compounds generally have IC50's below 1 μM in the enzyme assay and several examples have EC50's below 2 μM in the cell based assay.

Compound names in the examples were generated using software from ACDLabs (version 8.0).

i) In-Vitro HCV NS5B Enzyme Inhibition Assay

WO 96/37619 describes the production of recombinant HCV RdRp from insect cells infected with recombinant baculovirus encoding the enzyme. The purified enzyme was shown to possess in vitro RNA polymerase activity using RNA as template. The reference describes a polymerisation assay using poly(A) and oligo(U) as a primer or an heteropolymeric template. Incorporation of tritiated UTP or NTPs is quantified by measuring acid-insoluble radioactivity. The present inventors have employed this assay to screen the various compounds described above as inhibitors of HCV RdRp.

Incorporation of radioactive UMP was measured as follows. The standard reaction (50 μl) was carried out in a buffer containing 20 mM tris/HCl pH 7.5, 5 mM MgCl$_2$, 1 mM DTT, 50 mM NaCl, 0.03% N-octylglucoside, 1 μCi [$^3$H]-UTP (40 Ci/mmol, NEN), 10 μM UTP and 10 μg/ml poly(A) or 5 μM NTPs and 5 μg/ml heteropolymeric template. Oligo(U)$_{12}$ (1 μg/ml, Genset) was added as a primer in the assay working on Poly(A) template. The final NS5B enzyme concentration was 5 nM. The order of assembly was: 1) compound, 2) enzyme, 3) template/primer, 4) NTP. After 1 h incubation at 22° C. the reaction was stopped by adding 50 μl of 20% TCA and applying samples to DE81 filters. The filters were washed thoroughly with 5% TCA containing 1M Na$_2$HPO$_4$/NaH$_2$PO$_4$, pH 7.0, rinsed with water and then ethanol, air dried, and the filter-bound radioactivity was measured in the scintillation counter. Carrying out this reaction in the presence of various concentrations of each compound set out above allowed determination of IC$_{50}$ values by utilising the formula:

$$\% \text{ Residual activity} = 100/(1+[I]/IC_{50})^s$$

where [I] is the inhibitor concentration and "s" is the slope of the inhibition curve.

ii) Cell Based HCV Replication Assay

Cell clones that stably maintain subgenomic HCV replicon were obtained by transfecting Huh-7 cells with an RNA replicon identical to I$_{377}$neo/NS3-3'/wt described by Lohmann et al. (1999) (EMBL-GENBANK No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in published International application WO 02/59321). Cells were seeded into 96 well plates at a density of 10$^4$ cells per well in a final volume of 0.1 ml of DMEM/10% FCS. Two hours after plating, 50 μl of DMEM/10% FCS containing a 3× concentration of inhibitor were added, cells were incubated for 96 hours and then fixed for 10' with ice-cold isopropanol. Each condition was tested in duplicate and average absorbance values were used for calculations. The cells were washed twice with PBS, blocked with 5% non-fat dry milk in PBS+0.1% Triton X100+0.02% SDS (PBSTS) and then incubated o/n at 4° C. with the 10E5/24 mab diluted in MiLk/PBSTS. After washing 5 times with PBSTS, the cells were incubated for 3 hours at room temperature with Fc specific anti-mouse IgG conjugated to alkaline phosphatase (Sigma), diluted in Milk/PBSTS. After washing again as above, the reaction was developed with p-Nitrophenyl phosphate disodium substrate (Sigma) and the absorbance at 405/620 nm read at intervals. For calculations, we used data sets where samples incubated without inhibitors had absorbance values comprised between 1 and 1.5. The inhibitor concentration that reduced by 50% the expression of NS3 (IC$_{50}$) was calculated by fitting the data to the Hill equation, $$\text{Fraction inhibition} = 1-(A_i-b)/(A_0-b) = [I]^n/([I]^n+IC_{50})$$

where
  $A_i$=absorbance value of HBI10 cells supplemented with the indicated inhibitor concentration.
  $A_0$=absorbance value of HBI10 cells incubated without inhibitor.
  b=absorbance value of Huh-7 cells plated at the same density in the same microtiter plates and incubated without inhibitor.
  n=Hill coefficient.

iii) General Procedures

All solvents were obtained from commercial sources (Fluka, puriss.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al., J. Org. Chem. 1978, 43, 2923) or on commercial flash chromatography systems (BIOTAGE Corporation and JONES FLASHMASTER II) utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H NMR spectra were recorded on BRUKER AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in hertz (Hz); number of protons. Mass spectral (MS) data were obtained on a PERKIN ELMER API 100, or WATERS MICROMASS ZQ, operating in negative (ES$^-$) or positive (ES$^+$) ionization mode and results are reported as the ratio of mass over charge (m/z) for the parent ion only. Preparative scale HPLC separations were carried out on a WATERS DELTA PREP 4000 separation module, equipped with a WATERS 486 absorption detector or on an automated WATERS FRACTION LYNX or GILSON preparative system. In all cases compounds were eluted with linear gradients of water and MeCN both containing 0.1% TFA using flow rates between 15 and 40 mL/min.

The following abbreviations are used in the examples, the schemes and the tables: Ac: acetyl; aq.: aqueous; Ar: aryl; atm: atmosphere; cat.: catalytic; dioxan(e): 1,4-dioxane; dppf: (1,1'-bisdiphenylphosphino)ferrocene; 1,2-DCE: 1,2- dichloroethane; DCM: dichloromethane; DIPEA: diisopropylethyl amine; DMAP: N,N-dimethylpyridin-4-amine; DME: dimethoxyethane; DMF: dimethylformamide; DMS: dimethylsulfide; DMSO: dimethylsulfoxide; DMP: Dess-Martin Periodinane; EDAC.HCl: 1-ethyl-(3-dimethylaminopropyl)carbodiimide HCl salt; eq.: equivalent(s); $Et_3N$: triethylamine; EtOAc: ethyl acetate; $Et_2O$: diethyl ether; EtOH: ethanol; $Et_3SiH$: triethylsilane; FC: Flash Chromatography; h: hour(s); HOAc: acetic acid; HATU: O-(7-azabenzotriazol-1-yl)-N,N,N',N'-tetramethyluronium hexafluorophosphate; Me: methyl; MeCN: acetonitrile; MeOH: methanol; min: minutes; MS: mass spectrum; NBS: N-bromo succinimide; PE: petroleum ether; Ph: phenyl; quant.: quantitative; RP-HPLC: reversed phase high-pressure liquid chromatography; RT: room temperature; sat.: saturated; sec: second(s); SFC: Super-critical fluid chromatography; s.s.: saturated solution; TBAF: tetrabutyl ammonium fluoride; TBTU: O-benzotriazol-1-yl-N,N,N',N'-tetramethyluronium tetrafluoroborate; TFA: trifluoroacetic acid; THF: tetrahydrofuran; THP: tetrahydropyranyl; TMS: trimethylsilyl.

Example 1

10-cyclohexyl-2-(dimethylamino)-1,2,3,3a,4,14b-hexahydrocyclopenta[d]indolo[2,1-a][2]benzazepine-7-carboxylic acid Step 1: benzyl 4-(aminosulfonyl)butanoate $Cs_2CO_3$ (0.51 eq) was added to a solution of 4-(aminosulfonyl)butanoic acid (1 M) in DMF. After 1 h, benzyl bromide (1 eq) was introduced and the reaction left to stir overnight before diluting with DCM and filtering. The filtered liquor was concentrated in vacuo, the residue taken up in DCM and washed with saturated aqueous $NaHCO_3$, water and brine, before being dried over $Na_2SO_4$, filtered and concentrated in vacuo. Trituration of the residue with $Et_2O$ afforded the title compound as a white solid (27%). $(ES^+)$ m/z 280 $(M+Na)^+$ Step 2: tert-butyl (2R)-2-({[(4-nitrophenyl)sulfonyl]oxy}methyl)aziridine-1-carboxylate A solution of tert-butyl (2R)-2-({[tert-butyl(dimethyl)silyl]oxy}methyl)aziridine-1-carboxylate (prepared following literature procedures: Travins, J. M.; Etzkorn, F. A. *Tetrahedron Lett.* 1998, 39, 9389-9392) in $THF/Et_2O$ (1/1) (0.17 M) was cooled in an ice bath and treated dropwise over 20 min with 1 M TBAF in THF (1.05 eq). The resulting solution was stirred in the ice bath for 30 min, before being quenched by the addition of sat. aq. $NaHCO_3$ and extracted into $Et_2O/PE$ (4/1). The organic layers were collected, washed with brine, dried over $Na_2SO_4$, filtered and concentrated in vacuo. The residue was taken up in dry DCM (0.17 M) and TEA (1.3 eq) introduced prior to cooling to 0° C. DMAP (0.1 eq) and 4-nitrobenzenesulfonyl chloride (1.1 eq) were added and the resulting mixture left to stir at RT overnight. The reaction mixture was diluted with DCM and washed with sat. aq. $NaHCO_3$, water and brine before drying over $Na_2SO_4$, filtering and concentrating in vacuo. The crude was purified by FC (PE/EtOAc 80:20) to afford the title compound as an off-white solid (57%). $(ES^+)$ m/z 359 $(M+H)^+$ Step 3: methyl (7R)-7-[(tert-butoxycarbonyl)amino]-14-cyclohexyl-7,8-dihydro-6H-indolo[1,2-e][1,5]benzoxazocine-11-carboxylate A solution of methyl 3-cyclohexyl-2-(2-hydroxyphenyl)-1H-indole-6-carboxylate (prepared as described in international patent application WO2006/046030) (0.15 M) in DMF was treated with CsF (4 eq) in one portion; the resulting mixture was stirred for 20 min at RT then treated via dropping funnel over 30 min with a solution of tert-butyl (2R)-2-({[(4-nitrophenyl)sulfonyl]oxy}methyl)aziridine-1-carboxylate (1.3 eq) in DMF (0.5 M). The resulting solution was stirred at RT overnight. The reaction mixture was then placed into an ice bath and powdered $KO^tBu$ (1.4 eq) added slowly to the reaction mixture. After 1.5 h, the reaction was quenched with sat. aq. $NH_4Cl$ and extracted into EtOAc. The combined organic layers were washed with water and brine, before being dried over $Na_2SO_4$, filtered and concentrated in vacuo. The crude material was purified by FC (PE/EtOAc 80:20) affording the product as an off-white foam (85%). $(ES^+)$ m/z 505 $(M+H)^+$ Step 4: methyl (7R)-7-amino-14-cyclohexyl-7,8-dihydro-6H-indolo[1,2-e][1,5]benzoxazocine-11-carboxylate Methyl (7R)-7-[(tert-butoxycarbonyl)amino]-14-cyclohexyl-7,8-dihydro-6H-indolo[1,2-e][1,5]benzoxazocine-11-carboxylate (0.14 M) in DCM was treated with TFA (10 eq) and stirred at RT for 1 h. The reaction was diluted with DCM and cautiously basified with aq. $NaHCO_3$, before separating the phases and extracting the aqueous with DCM. The combined organics were washed with brine, dried over $Na_2SO_4$, filtered and concentrated in vacuo to afford the product as an off-white foam (100%) that was used without further purification. $(ES^+)$ m/z 405 $(M+H)^+$; $[\alpha]_D$ +42.3, c=1, MeOH Step 5: methyl (7R)-14-cyclohexyl-7-(methylamino)-7,8-dihydro-6H-indolo[1,2-e][1,5]benzoxazocine-11-carboxylate A solution of methyl (7R)-7-amino-14-cyclohexyl-7,8-dihydro-6H-indolo[1,2-e][1,5]benzoxazocine-11-carboxylate (0.35 M) in THF was treated drop-wise with 2,2,2-trifluoroethyl formate (1.2 eq) and stirred overnight at RT. The volatiles were removed in vacuo and the residue dissolved (0.11 M) in THF and treated drop-wise with $BH_3$.DMS complex (2 M in THF; 5 eq). The resulting solution was stirred at RT for 20 h. The reaction was quenched by the careful addition of HCl/MeOH (1.25 M) and the resulting solution refluxed for 2 h. The volatiles were then removed in vacuo and the residue partitioned between sat. aq. $NaHCO_3$ and EtOAc. The combined organics were washed with brine, dried over $Na_2SO_4$, filtered and concentrated in vacuo. The crude was purified by FC (EtOAc/PE 80:20+1% $NEt_3$) to afford the product (79%). $(ES^+)$ m/z 419 $(M+H)^+$; $[\alpha]_D$ +47.4, c=0.46, $CHCl_3$ Step 6: methyl (7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylate To a solution of tert-butyl (2-oxoethyl)carbamate (1 eq; 0.38 M) in dry methanol was added a mixture of methyl (7R)-14-cyclohexyl-7-(methylamino)-7,8-dihydro-6H-indolo[1,2-e][1,5]benzoxazocine-11-carboxylate (0.14 M), acetic acid (2 eq) and sodium acetate (1 eq) in dry methanol, and the mixture stirred at RT for 15 min. Then Pd/C (0.3 weight eq) was added as a slurry in MeOH under $N_2$. The atmosphere in the reaction vessel was charged with $H_2$ and the reaction stirred vigorously under a $H_2$ atmosphere (balloon) at 60° C. overnight. The reaction was allowed to cool to RT, flushed with $N_2$ and filtered through a plug of CELITE. The filtrate was concentrated in vacuo and the residue purified by FC (PE/EtOAc 2.5:1 to 1.5:1 gradient) to afford the title compound (82%). (ES$^+$) m/z 562 (M+H)$^+$; [α]$_D$+67.1, c=0.67, CHCl$_3$ Step 7: (7R)-7-[{2-[(tert-butoxycarbonyl)amino]
ethyl}(methyl)amino]-14-cyclohexyl-7,8-dihydro-
6H-indolo[1,2-e][1,5]benzoxazocine-11-carboxylic
acid Lithium hydroxide monohydrate (4.4 eq) was added to a solution of methyl (7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylate (0.02 M) in MeOH/THF/H$_2$O (1/1/1). The reaction was heated at 60° C. for 4 h prior to introducing further lithium hydroxide monohydrate (5 eq) and continuing heating for 2 h. The reaction was allowed to cool to RT, and the solvent volume reduced in vacuo. The residue was partitioned between 1N HCl (aq) and EtOAc, extracting the aqueous fraction a further two times with EtOAc. The combined organics were washed with brine, dried over Na$_2$SO$_4$, filtered and concentrated in vacuo to afford the product as an off white foam (98%). (ES$^+$) m/z 548 (M+H)$^+$ Step 8: benzyl 4-{[({7R)-7-[{2-[(tert-butoxycarbo-
nyl)amino]ethyl}(methyl)amino]-14-cyclohexyl-7,8-
dihydro-6H-indolo[1,2-e][1,5]benzoxazocin-11-
yl}carbonyl)amino]sulfonyl}butanoate Benzyl 4-(aminosulfonyl)butanoate (1.3 eq) (prepared as described in step 1), DMAP (2.5 eq) and EDAC.HCl (1.5 eq), were added to a solution of (7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylic acid (0.03 M) in DCM. The reaction was stirred under N$_2$ at RT for 24 h, before volatiles were removed in vacuo to leave the crude product as a yellow gum which was purified by automated RP-HPLC (WATERS XTERRA column; MeCN/H$_2$O/0.1% TFA gradient). Fractions containing the pure compound were combined and lyophilized to afford the product as a white powder (37%). (ES$^+$) m/z 787 (M+H)$^+$ Step 9: 4-{[({(7R)-7-[{2-[(tert-butoxycarbonyl)
amino]ethyl}(methyl)amino]-14-cyclohexyl-7,8-
dihydro-6H-indolo[1,2-e][1,5]benzoxazocin-11-yl-
carbonyl)amino]sulfonyl}butanoic acid Pd/C (10 wt %) was added as a slurry in MeOH under N$_2$ to a solution of benzyl 4-{[({(7R)-7-[{2-[(tert-butoxycarbonyl)amino]ethyl}(methyl)amino]-14-cyclohexyl-7,8-dihydro-6H-indolo[1,2-e][1,5]benzoxazocin-11-yl}carbonyl)amino]sulfonyl}butanoate (0.003 M) in MeOH. The atmosphere in the reaction vessel was exchanged for H$_2$ and the reaction stirred vigorously at RT for 1 h. The reaction vessel was flushed with N$_2$ and the reaction mixture filtered through a plug of CELITE (washing well with MeOH). Volatiles were removed in vacuo to afford the crude product as a yellow oil. (ES$^+$) m/z 697 (M+H)$^+$ Step 10: 4-{[({(7R)-7-[(2-aminoethyl)(methyl)
amino]-14-cyclohexyl-7,8-dihydro-6H-indolo[1,2-e]
[1,5]benzoxazocin-11-yl}carbonyl)amino]
sulfonyl}butanoic acid 4-{[({(7R)-7-[{2-[(tert-butoxycarbonyl)amino]ethyl}(methyl)amino]-14-cyclohexyl-7,8-dihydro-6H-indolo[1,2-e][1,5]benzoxazocin-11-yl}carbonyl)amino]sulfonyl}butanoic acid was dissolved in DCM (0.01 M), and ethereal HCl added (2M, >100 eq). The reaction was stirred with heating at 40° C. for 1 h. Volatiles were removed in vacuo, and the residue diluted with Et$_2$O and reconcentrated in vacuo (twice) to drive off excess HCl and afford the crude product as the bis hydrochloride salt. (ES$^+$) m/z 597 (M+H)$^+$ Step 11: (7R)-14-cyclohexyl-25-methyl-7,8-dihydro-
6H-7,11-(epiminoethanoiminobutan-
othioiminomethano)indolo[1,2-e][1,5]benzoxazo-
cine-15,21-dione 17,17-dioxide DIPEA (6 eq) and HATU (1.2 eq) were introduced to a solution of 4-{[({(7R)-7-[(2-aminoethyl)(methyl)amino]-14-cyclohexyl-7,8-dihydro-6H-indolo[1,2-e][1,5]benzoxazocin-11-yl}carbonyl)amino]sulfonyl}butanoic acid (0.005 M) in DMF and the reaction stirred under N$_2$ at 45° C. for 1 h. The volatiles were evaporated in vacuo and the residue purified by automated RP-HPLC (WATERS XTERRA column; MeCN/H$_2$O/0.1% TFA gradient). Fractions containing the pure compound were combined and lyophilized to afford the product as a white powder (30% overall for steps 4, 5, 6). $^1$H NMR (600 MHz, DMSO-d$_6$+TFA, 335 K) δ1.14-1.22 (m, 1H), 1.31-1.40 (m, 2H), 1.53-1.57 (m, 1H), 1.68-1.75 (m, 2H), 1.84-1.87 (m, 1H), 1.91-2.07 (m, 5H), 2.10-2.16 (m, 1H), 2.29-2.34 (m, 1H), 2.38-2.45 (m, 1H), 2.71-2.77 (m, 1H), 2.94 (s, 3H), 3.37-3.55 (m, 6H), 3.88-3.95 (m, 1H), 4.26-4.31 (m, 1H), 4.36-4.42 (m, 1H), 4.81-4.86 (m, 1H), 7.28-7.32 (m, 2H), 7.38 (dd, J 7.7, 1.5, 1H), 7.47 (d, J 8.7, 1H), 7.54-7.57 (m, 1H), 7.92 (d, J 8.7, 1H), 8.16 (s, 1H), 8.19 (b s, 1H), 11.57 (b s, 1H); (ES$^+$) m/z 579 (M+H)$^+$.

Example 2

(7R)-14-cyclohexyl-24-methyl-7,8-dihydro-6H-7,11-
(epiminoethanoiminopropanothioiminomethano)
indolo[1,2-e][1,5]benzoxazocin-15-one 17,17-diox-
ide Step 1: 3-chloropropane-1-sulfonamide A 0.5 M solution of ammonia (15 eq) in dioxane was added slowly at RT under nitrogen to a solution of 3-chloropropane sulfonyl chloride in dioxane (0.56 M). The reaction was left to stir for 2 h before removing volatiles in vacuo. The residue was taken up in CHCl$_3$, filtered to remove ammonium chloride and the filtered liquor concentrated in vacuo to afford the title compound as a colourless oil that solidified on standing. $^1$H NMR (300 MHz, DMSO-d$_6$, 300 K) δ2.09-2.17 (m, 2H), 3.06-3.11 (m, 2H), 3.72-3.77 (m, 2H), 6.87 (s, 2H).

Step 2: tert-butyl {2-[[(7R)-11-({[(3-chloropropyl)
sulfonyl]amino}carbonyl)-14-cyclohexyl-7,8-dihy-
dro-6H-indolo[1,2-e][1,5]benzoxazocin-7-yl](me-
thyl)amino]ethyl}carbamate 3-chloropropane-1-sulfonamide (1.8 eq), DMAP (2.9 eq) and EDAC.HCl (1.8 eq) were added to a solution of (7R)-7-[{2-[(tert-butoxycarbonyl)amino]ethyl}(methyl)amino]-14- cyclohexyl-7,8-dihydro-6H-indolo[1,2-e][1,5]benzoxazocine-11-carboxylic acid (prepared as described in Example 1, Step 7) (0.025 M) in DCM. The reaction was stirred under $N_2$ at 40° C. for 2 h, before being allowed to cool. Volatiles were removed in vacuo to leave the crude product as a yellow gum which could be taken on without further purification. (ES$^+$) m/z 687 (M+H)$^+$; 689 (M+H)$^+$

Step 3: (7R)-7-[(2-aminoethyl)(methyl)amino]-N-[(3-chloropropyl)sulfonyl]-14-cyclohexyl-7,8-dihydro-6H-indolo[1,2-e][1,5]benzoxazocine-11-carboxamide tert-butyl {2-[[(7R)-11-({[(3-chloropropyl)sulfonyl]amino}carbonyl)-14-cyclohexyl-7,8-dihydro-6H-indolo[1,2-e][1,5]benzoxazocin-7-yl](methyl)amino]ethyl}carbamate was dissolved in DCM (0.025 M), and ethereal HCl added (2M, >50 eq). The reaction was stirred with heating at 40° C. for 1 h. Volatiles were removed in vacuo, and the residue diluted with $Et_2O$ and reconcentrated in vacuo (twice) to drive off excess HCl and afford the crude product as the bis hydrochloride salt. Purification was by automated RP-HPLC (Waters xterra column; MeCN/$H_2O$/0.1% TFA gradient). Fractions containing the pure compound were combined and lyophilized to afford the product as a white powder (37% over steps 2, 3). (ES$^+$) m/z 587 (M+H)$^+$; 589 (M+H)$^+$

Step 4: (7R)-14-cyclohexyl-24-methyl-7,8-dihydro-6H-7,11-(epiminoethanoiminopropanothioiminomethano)indolo[1,2-e][1,5]benzoxazocin-15-one 17,17-dioxide $^i$Pr$_2$NEt (20 eq) was added to a solution of (7R)-7-[(2-aminoethyl)(methyl)amino]-N-[(3-chloropropyl)sulfonyl]-14-cyclohexyl-7,8-dihydro-6H-indolo[1,2-e][1,5]benzoxazocine-11-carboxamide in MeCN (0.003 M). The reaction was heated in a microwave at 150° C. for 300 sec. The volatiles were removed in vacuo and the residue was purified by automated RP-HPLC (Waters xterra column; MeCN/$H_2O$/0.1% TFA gradient). Fractions containing the pure compound were combined and lyophilized to afford the product as a white powder (8.5%). $^1$H NMR (400 MHz, DMSO-d$_6$, 300 K) δ1.10-1.20 (m, 1H), 1.28-1.37 (m, 2H), 1.42-1.47 (m, 1H), 1.65-1.73 (m, 2H), 1.81-2.09 (m, 5H), 2.17-2.28 (m, 1H), 2.31 (s, 3H), 2.62-2.69 (m, 1H), 2.80-2.91 (m, 1H), 3.02-3.18 (m, 3H), 3.44-3.62 (m, 5H), 3.84 (dd, J 14.8, 9.4, 1H), 4.02 (t, J 11.4, 1H), 4.34 (dd, J 11.4, 5.4, 1H), 4.54 (d, J 14.8, 1H), 7.31-7.38 (m, 3H), 7.48 (d, J 8.4, 1H), 7.54-7.59 (m, 1H), 7.92 (d, J 8.4, 1H), 8.09 (s, 1H), 8.65 (b s, 1H), 11.85 (b s, 1H); (ES$^+$) m/z 551 (M+H)$^+$.

Example 3

(7R)-14-cyclohexyl-21,24-dimethyl-7,8-dihydro-6H-7,11-(epiminoethanoiminopropanothioiminomethano)indolo[1,2-e][1,5]benzoxazocin-15-one 17,17-dioxide Formaldehyde (37 wt % in water; 15 eq) was added to a solution of (7R)-14-cyclohexyl-24-methyl-7,8-dihydro-6H-7,11-(epiminoethanoiminopropanothioiminomethano)indolo[1,2-e][1,5]benzoxazocin-15-one 17,17-dioxide (prepared as described in Example 2; Step 4) in MeOH (0.004 M). The pH was adjusted to pH 5-6 with AcOH and, after 5 min, NaBH (20 eq) introduced. The reaction was stirred at RT for 15 min before quenching with 1N HCl (aq) and concentrating to dryness in vacuo. The residue was purified by automated RP-HPLC (Waters xterra column; MeCN/$H_2O$/0.1% TFA gradient). Fractions containing the pure compound were combined and lyophilized to afford the product as a white powder (65%). $^1$H NMR (400 MHz, DMSO-d$_6$, 300 K) δ1.10-1.20 (m, 1H), 1.29-1.38 (m, 2H), 1.42-1.46 (m, 1H), 1.67-1.74 (m, 2H), 1.83-1.94 (m, 4H), 2.12-2.29 (m, 2H), 2.33 (s, 3H), 2.63-2.69 (m, 1H), 2.80 (s, 3H), 2.84-2.95 (m, 1H), 3.08-3.20 (m, 3H), 3.44-3.68 (m, 5H), 3.84 (dd, J 14.9, 9.8, 1H), 4.02 (t, J 11.7, 1H), 4.29 (dd, J 11.7, 5.2, 1H), 4.53 (d, J 14.9, 1H), 7.31-7.39 (m, 3H), 7.49 (d, J 8.4, 1H), 7.54-7.59 (m, 1H), 7.93 (d, J8.4, 1H), 8.11 (s, 1H), 11.98 (s, 1H); (ES$^+$) m/z 565 (M+H)$^+$.

Example 4

(7R)-14-[(1R,2S) or (1S,2R)-2-fluorocyclohexyl]-21,24-dimethyl-7,8-dihydro-6H-7,11-(epiminoethanoiminopropanothioiminomethano)indolo[1,2-e][1,5]benzoxazocin-15-one 17,17-dioxide

Step 1: methyl 3-cyclohex-1-en-1-yl-1H-indole-6-carboxylate

A solution (0.1 M) of 3-cyclohex-1-en-1-yl-1H-indole-6-carboxylic acid (prepared as described in published International patent application WO 2004/087714) in dry DMF was cooled to 0° C. and treated with $K_2CO_3$ (1.05 eq). A solution (3 M) of MeI (1.05 eq) in DMF was then added over 0.5 h and the temperature was raised to 20° C. After 18 h the reaction was quenched with aqueous HCl (1 N) and diluted with EtOAc. The organic phase was separated and washed several times with aqueous HCl (1 N), then with brine. The dried organics were concentrated to give the title compound (99%) as a solid; (ES$^+$) m/z 256 (M+H)$^+$.

Step 2: (±)-methyl 3-[(trans)-2-hydroxycyclohexyl]-1H-indole-6-carboxylate

A solution (0.2 M) of the preceding material in dry THF was treated over 1 h at 0° C. with $BH_3$.SMe$_2$ (2 M in THF, 1.1 eq). The mixture was stirred at 20° C. for 12 h, then cooled to 0° C. and treated sequentially with aqueous NaOH (3 M, 5.7 eq) and $H_2O_2$ (30% in $H_2O$ 8.4 eq). This mixture was stirred at 20° C. for 3 h then diluted with EtOAc and neutralized with s.s. $NH_4Cl$. The organic phase was washed with s.s. $NaHCO_3$ and brine, then dried and concentrated. The residue was washed several times with $Et_2O$ to give the title compound (73%) as a white powder; (ES$^+$) m/z 274 (M+H)$^+$.

Step 3: (±)-methyl 3-[(trans)-2-fluorocyclohexyl]-1H-indole-6-carboxylate

A solution (0.08 M) of the foregoing material in dry EtOAc was treated with DAST (1.2 eq) over 15 min at −50° C. The mixture was stirred for 1 h then warmed to 20° C. After 3 h the mixture was quenched with s.s. $NaHCO_3$ and diluted with EtOAc. The organic phase was washed with brine, dried and concentrated under reduced pressure. The residue was crystallized from hot EtOAc to give the title compound (61%). The filtrate was concentrated and the residue purified by flash chromatography (10% to 30% EtOAc: PE) to give a second crop of the title compound (17%) as a solid; (ES$^+$) m/z 276 (M+H)$^+$.

Step 4: (±)-methyl 2-bromo-3-[(trans)-2-fluorocyclohexyl]-1H-indole-6-carboxylate A solution (0.16 M) of the foregoing material in CH$_2$Cl$_2$ was treated with NBS (1.1 eq) over 2 h. The resulting mixture was stirred for 4 h then diluted with aqueous Na$_2$S$_2$O$_3$ (1 N) and stirred for 12 h. The organic phase was separated and washed with aqueous Na$_2$S$_2$O$_3$ (1 N) and brine. The dried organics were concentrated to afford a residue that was purified by flash chromatography (1:9 to 2:8 EtOAc:PE) to give the title compound (56%) as a pale solid; (ES$^+$) m/z 354 (M+H)$^+$.

Step 5: methyl 2-bromo-3-[(1R,2S)-2-fluorocyclohexyl]-1H-indole-6-carboxylate and methyl 2-bromo-3-[(1S,2R)-2-fluorocyclohexyl]-1H-indole-6-carboxylate The preceding material was dissolved in MeOH and the enantiomers were separated by SFC chromatography (stationary phase: CHIRALCEL OJ-H 250×10 mm; mobile phase: 25% MeOH containing 0.2% diethylamine/CO$_2$; flow rate 10 mL/min; column pressure: 100 bar; column temperature: 35° C.; detection UV 254 nm). The enantiomeric excess of the two fractions thus obtained (compound recovery 95%) were determined by chiral phase analytical HPLC (stationary phase: CHIRALPAK AD 250×4.6 mm; mobile phase 95:5 n-hexane:isopropyl alcohol containing 0.2% TFA; flow rate 1 mL/min; detection: JV 300 nM; sample concentration: 1 mg/mL; injection volume 10 uL): Isomer A (retention time 37.82 min, e.e. 99.8%, $[\alpha]_D^{20}$=−8.0 (c=0.77, CHCl$_3$)); Isomer B (retention time 43.89 min, 99%, $[\alpha]_D^{20}$=+8.0 (c=0.77, CHCl$_3$)).

Step 6: methyl 3-[(1R,2S) or (1S,2R)-2-fluorocyclohexyl]-2-(2-hydroxyphenyl)-1H-indole-6-carboxylate A solution (0.16 M) of (−)-methyl 2-bromo-3-[(trans)-2-fluorocyclohexyl]-1H-indole-6-carboxylate (isomer A from Step 5, above) in dioxane was treated with aqueous Na$_2$CO$_3$ (2 N, 4.6 eq), 2-hydroxyphenylboronic acid (1.8 eq) and Pd(PPh$_3$)$_4$ (0.1 eq). The mixture was stirred at 80° C. for 2 h, then diluted with EtOAc, washed with aqueous HCl (1 N) and brine. The dried organic layer was concentrated in vacuo to give a residue that was purified by flash chromatography (8:2 PE:EtOAc) to give the title compound (90%) as a solid. $^1$H NMR (300 MHz, DMSO-d$_6$, 300 K) δ 1.21-1.65 (m, 3H), 1.68 (m, 4H), 2.05-2.19 (m, 1H), 2.75-2.97 (m, 1H), 3.87 (s, 3H), 5.00 (dm, J$_{HF}$ 49.0, 1H), 6.93 (t, J 7.5, 1H), 7.01 (d, J 7.5, 1H), 7.28 (t, J 7.5, 1H), 7.29 (d, J7.5, 1H), 7.59 (d, J8.4, 1H), 7.82 (d, J8.4, 1H), 8.02 (s, 1H), 9.74 (s, 1H), 11.34 (s, 1H).

Step 7: methyl (7R)-7-[(tert-butoxycarbonyl)amino]-14-[(1R,2S) or (1S,2R)-2-fluorocyclohexyl]-7,8-dihydro-6H-indolo[1,2-e][1,5]benzoxazocine-11-carboxylate The preceding material was treated as described in Example 1, Step 3 to furnish the title compound (96%) as a pale yellow oil. (ES$^+$) m/z 523 (M+H)$^+$

Step 8: methyl (7R)-7-amino-14-[(1R,2S) or (1S,2R)-2-fluorocyclohexyl]-7,8-dihydro-6H-indolo[1,2-e][1,5]benzoxazocine-11-carboxylate The preceding material was treated as described in Example 1, Step 4 to furnish the title compound (100%) as a yellow foam. (ES$^+$) m/z 423 (M+H)$^+$

Step 9: methyl (7R)-14-[(1R,2S) or (1S,2R)-2-fluorocyclohexyl]-7-(methylamino)-7,8-dihydro-6H-indolo[1,2-e][1,5]benzoxazocine-11-carboxylate The preceding material was treated as described in Example 1, Step 5 to furnish the title compound (73%) as a yellow foam. (ES$^+$) m/z 437 (M+H)$^+$

Step 10: methyl (7R)-7-[{2-[(tert-butoxycarbonyl)amino]ethyl}(methyl)amino]-14-(1R,2S) or (1S,2R)-2-fluorocyclohexyl]-7,8-dihydro-6H-indolo[1,2-e][1,5]benzoxazocine-11-carboxylate The preceding material was treated as described in Example 1, Step 6 to furnish the title compound (80%). (ES$^+$) m/z 580 (M+H)$^+$

Step 11: (7R)-7-[{2-[(tert-butoxycarbonyl)amino]ethyl}(methyl)amino]-14-[(1R,2S) or (1S,2R)-2-fluorocyclohexyl]-7,8-dihydro-6H-indolo[1,2-e][1,5]benzoxazocine-11-carboxylic acid The preceding material was treated as described in Example 1, Step 7 to furnish the title compound (80%). (ES$^+$) m/z 566 (M+H)$^+$

Step 12: tert-butyl {2-[{(7R)-11-({[(3-chloropropyl)sulfonyl]amino}carbonyl)-14-[(1R,2S) or (1S,2R)-2-fluorocyclohexyl]-7,8-dihydro-6H-indolo[1,2-e][1,5]benzoxazocin-7-yl}(methyl)amino]ethyl}carbamate The preceding material was treated as described in Example 2, Step 2 to furnish the title compound used as crude in the next step. (ES$^+$) m/z 705 (M+H)$^+$; 707 (M+H)$^+$

Step 13: (7R)-7-[(2-aminoethyl)(methyl)amino]-N-[(3-chloropropyl)sulfonyl]-14-[(1R,2S) or (1S,2R)-2-fluorocyclohexyl]-7,8-dihydro-6H-indolo[1,2-e][1,5]benzoxazocine-11-carboxamide The preceding material was treated as described in Example 2, Step 3 to furnish the title compound (39% two steps). (ES$^+$) m/z 605 (M+H)$^+$; 607 (M+H)$^+$

Step 14: (7R)-14-[(1R,2S) or (1S,2R)-2-fluorocyclohexyl]-24-methyl-7,8-dihydro-6H-7,11-(epiminoethanoiminopropanothioiminomethano)indolo[1,2-e][1,5]benzoxazocin-15-one 17,17-dioxide The preceding material was treated as described in Example 2, Step 4 to furnish the title compound (4%). (ES$^+$) m/z 569 (M+H)$^+$.

Step 15: (7R)-14-[(1R,2S)) or (1S,2R)-2-fluorocyclohexyl]-21,24-dimethyl-7,8-dihydro-6H-7,11-(epiminoethanoiminopropanothioiminomethano)indolo[1,2-e][1,5]benzoxazocin-15-one 17,17-dioxide The preceding material was treated as described in Example 3, Step 1 to furnish the title compound (15%). $^1$H NMR (400 MHz, DMSO-d$_6$+TFA, 330 K) δ 1.00-1.40 (m, 2H), 1.50-1.70 (m, 4H), 1.70-1.80 (m, 1H), 1.90-2.10 (m, 1H), 2.20-2.40 (m, 3H), 2.30 (s, 3H), 2.85 (s, 3H), 3.10-3.40 (m, 3H), 3.40-3.80 (m, 6H), 3.90-4.00 (m, 1H), 4.00-4.10 (m, 1H), 4.30-4.40 (m, 1H), 4.55-4.70 (m, 1H), 4.95-5.10 (m, 1H), 7.25-7.35 (m, 2H), 7.45-7.60 (m, 3H), 7.95 (d, J 8.5, 1H), 8.16 (s, 1H); (ES$^+$) m/z 583 (M+H)$^+$.

The following tables show these examples:

TABLE 1

| Example no. | Compound name | Structure | procedure | m/z (ES$^+$) |
|---|---|---|---|---|
| 3 = 101 | (7R)-14-cyclohexyl-21,24-dimethyl-7,8-dihydro-6H-7,11-(epiminoethanoiminopropanothioiminomethano)indolo[1,2-e][1,5]benzoxazocin-15-one 17,17-dioxide | | A, B | 565 |
| 2 = 102 | (7R)-14-cyclohexyl-24-methyl-7,8-dihydro-6H-7,11-(epiminoethanoiminopropanothioiminomethano)indolo[1,2-e][1,5]benzoxazocin-15-one 17,17-dioxide | | A | 551 |

16 membered macrocycles

TABLE 2

17 membered macrocycle

| Example no. | Compound name | Structure | procedure | m/z (ES+) |
|---|---|---|---|---|
| 1 = 201 | (7R)-14-cyclohexyl-25-methyl-7,8-dihydro-6H-7,11-(epiminoethanoiminobutanothio-iminomethano)indolo[1,2-e][1,5]benzoxazocine-15,21-dione 17,17-dioxide | 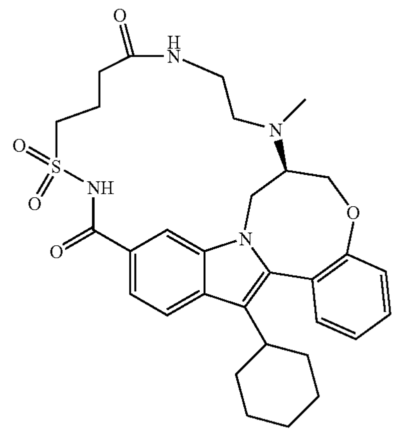 | A | 579 |

TABLE 3

2-Fluorocyclohexyl macrocycles

| Example no. | Compound name | Structure | procedure | m/z (ES+) |
|---|---|---|---|---|
| 4 = 301 | (7R)-14-[(1R,2S) or (1S,2R)-2-fluorocyclohexyl]-21,24-dimethyl-7,8-dihydro-6H-7,11-(epiminoethanoiminopropanothio-iminomethano)indolo[1,2-e][1,5]benzoxazocin-15-one 17,17-dioxide | 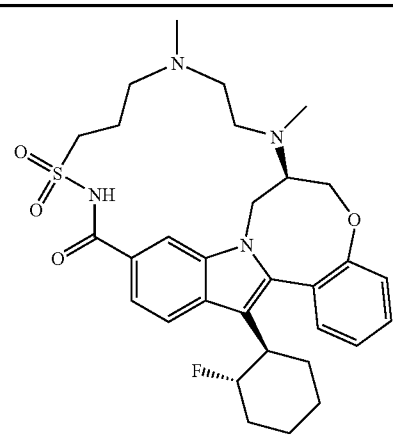 | A, B | 583 |

What is claimed is:

1. A compound of the formula (I):

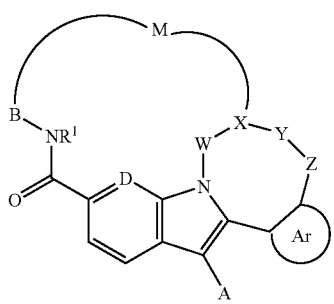

(I)

wherein

Ar is a moiety containing at least one aromatic ring and possesses 5-, 6-, 9- or 10-ring atoms optionally containing 1, 2 or 3 heteroatoms independently selected from N, O and S, which ring is optionally substituted by groups $Q^1$ and $Q^2$;

$Q^1$ is halogen, hydroxy, $C_{1-6}$alkyl, $C_{1-6}$alkoxy, aryl, heteroaryl, $CONR^aR^b$, $(CH_2)_{0-3}NR^aR^b$, $O(CH_2)_{1-3}NR^aR^b$, $O(CH_2)_{0-3}CONR^aR^b$, $O(CH_2)_{0-3}$aryl, $O(CH_2)_{0-3}$heteroaryl, $O(CR^eR^f)$aryl, $O(CR^eR^f)$heteroaryl or $OCHR^c R^d$;

$R^a$ and $R^b$ are each independently selected from hydrogen, $C_{1-4}$alkyl and $C(O)C_{1-4}$alkyl;

or $R^a$, $R^b$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

$R^c$ and $R^d$ are each independently selected from hydrogen and $C_{1-4}$alkoxy;

or $R^c$ and $R^d$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$R^e$ is hydrogen or $C_{1-6}$alkyl;

$R^f$ is $C_{1-6}$alkyl;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;

A is $C_{3-6}$alkyl or $C_{2-6}$alkenyl, or A is a non-aromatic ring of 3 to 8 ring atoms where said ring may contain a double bond and/or may contain a O, S, SO, $SO_2$ or NH moiety, or A is a non-aromatic bicyclic moiety of 4 to 8 ring atoms, and A is optionally substituted by halogen, hydroxy, $C_{1-4}$alkyl or $C_{1-4}$alkoxy;

D is N or $CR^g$;

$R^g$ is hydrogen, fluorine, chlorine, $C_{1-4}$alkyl, $C_{2-4}$alkenyl or $C_{1-4}$alkoxy, where said $C_{1-4}$alkyl, $C_{2-4}$alkenyl and $C_{1-4}$alkoxy groups are optionally substituted by hydroxy or fluorine;

W is a bond, C=O, O, $S(O)_{0-2}$ or $-(CR^{10}R^{11})-(CR^{12}R^{13})_{0-1}-$;

Y is a bond, C=O, O, $-CR^{14}R^{15}-$ or $NR^{14}$;

Z is a bond, C=O, O, $S(O)_{0-2}$, $-(CR^{10}R^{11})-(CR^{12}R^{13})_{0-1}-$ or $NR^{10}$;

and none, one or two of W, Y and Z are a bond;

X is $-CR^{14a}-$ or N;

$R^{10}$, $R^{11}$, $R^{12}$, $R^{13}$, $R^{14}$, $R^{14a}$ and $R^{15}$ are each independently selected from hydrogen, hydroxy, $C_{1-6}$alkyl, $C_{2-6}$alkenyl, $C_{1-6}$alkoxy, $C(O)C_{1-6}$alkyl, Het, $(CH_2)_{0-3}NR^{16}R^{17}$, $C(O)(CH_2)_{0-3}NR^{16}R^{17}$, $NHC(O)(CH_2)_{0-3}NR^{16}R^{17}$, $O(CH_2)_{1-3}NR^{16}R^{17}$, $S(O)_{0-2}(CH_2)_{0-3}R^{16}R^{17}$ and $C(O)(CH_2)_{0-3}OR^{16}$;

or one of $R^{10}$, $R^{14}$ and $R^{14a}$ is linked to $R^{22}$ or $R^{23}$ to form a ring of 4 to 10 atoms, where said ring is optionally substituted by halogen, hydroxy, $C_{1-4}$alkyl or $C_{1-4}$alkoxy;

Het is a heteroaliphatic ring of 4 to 7 ring atoms, which ring may contain 1, 2 or 3 heteroatoms selected from N, O or S or a group S(O), $S(O)_2$, NH or $NC_{1-4}$alkyl;

$R^{16}$ and $R^{17}$ are independently selected from hydrogen, $C_{1-6}$alkyl and $(CH_2)_{0-4}NR^{18}R^{19}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

$R^{18}$ and $R^{19}$ are independently selected from hydrogen and $C_{1-6}$alkyl;

or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

$R^1$ is hydrogen or $C_{1-6}$alkyl;

B is $-CR^{20}R^{21}-$, $-C(=O)-$, $-SO-$ or $-SO_2-$;

$R^{20}$ and $R^{21}$ are independently selected from hydrogen and $C_{1-6}$alkyl;

or $R^{20}$ and $R^{21}$, together with the carbon atom to which they are joined, form a $C_{3-6}$cycloalkyl group;

M is $C_{4-8}$alkylene or $C_{4-8}$alkenylene, optionally substituted by $R^{22}$, where 1, 2 or 3 of the carbon atoms in the $C_{4-8}$alkylene or $C_{4-8}$alkenylene groups is optionally replaced by O, $NR^{23}$, S, SO, $SO_2$, piperidinyl, piperazinyl or pyrrolidinyl, where $R^{23}$ is hydrogen or $C_{1-6}$alkyl, or $R^{23}$ is linked to one of $R^{10}$, $R^{14}$ and $R^{14a}$ to form a ring of 4 to 10 atoms as hereinbefore described;

where $R^{22}$ is halo, $C_{1-4}$alkyl, $(CH_2)_{0-3}C_{3-8}$cycloalkyl, $(CH_2)_{0-3}$aryl, $(CH_2)_{0-3}$heteroaryl, $(CH_2)_{0-3}$Het or oxo, or $R^{22}$ is linked to one of $R^{10}$, $R^{14}$ and $R^{14a}$ to form a ring of 4 to 10 atoms as hereinbefore described;

or a pharmaceutically acceptable salt thereof.

2. A compound according to claim 1 in which Ar is phenyl, 2-pyridyl, 3-pyridyl, 4-pyridyl, 2-furanyl or 3-furanyl, optionally substituted by groups $Q^1$ and $Q^2$ as defined in claim 1.

3. A compound according to claim 2 in which $Q^1$ is methoxy and $Q^2$ is absent.

4. A compound according to claim 1 in which A is cyclopentyl or cyclohexyl optionally substituted by halogen, hydroxy, $C_{1-4}$alkyl or $C_{1-4}$alkoxy.

5. A compound according to claim 1 in which D is $CR^g$ where $R^g$ is hydrogen or $C_{1-4}$alkyl.

6. A compound according to claim 1 in which W is $-CH_2-$ or $-CH_2CH_2-$.

7. A compound according to claim 1 in which W is Z is a bond, O, $-CH_2-$ or $-CH_2CH_2-$.

8. A compound according to claim 1 in which Y is $-CH_2-$, NH, $N(C_{1-4}alkyl)$, $N(CH_2)_2N(C_{1-4}alkyl)_2$ or $NC(O)CH_2N(C_{1-4}alkyl)_2$.

9. A compound according to claim 1 in which X is $-CH-$ or $-C(C_{1-6}alkyl)-$.

10. A compound according to claim 1 in which $R^1$ is hydrogen or methyl.

11. A compound according to claim 1 in which B is $-CH_2-$ or $-SO_2-$.

12. A compound according to claim 1 in which M is selected from:

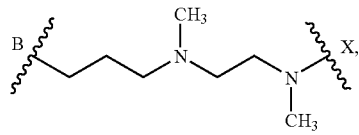

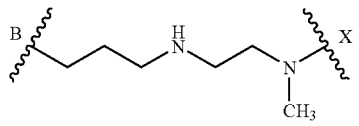

and

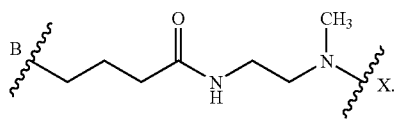

13. A compound according to claim 1 of the formula (Ia):

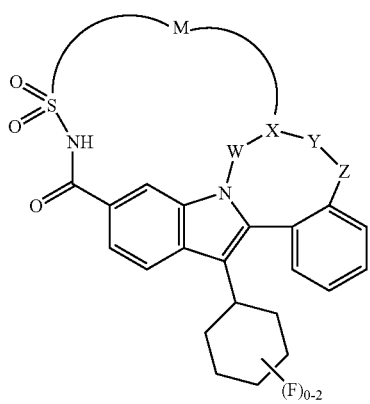

(Ia)

or a pharmaceutically acceptable salt thereof, wherein W, X, Y, Z and M are as defined in relation to formula (I).

14. A compound according to claim 1 selected from:
(7R)-14-cyclohexyl-21,24-dimethyl-7,8-dihydro-6H-7,11-(epiminoethanoiminopropanothio iminomethano)indolo[1,2-e][1,5]benzoxazocin-15-one 17,17-dioxide, (7R)-14-cyclohexyl-24-methyl-7,8-dihydro-6H-7,11-(epiminoethanoiminopropanothioimino methano)indolo[1,2-e][1,5]benzoxazocin-15-one 17,17-dioxide, (7R)-14-cyclohexyl-25-methyl-7,8-dihydro-6H-7,11-(epiminoethanoiminobutanothioimino methano)indolo[1,2-e][1,5]benzoxazocine-15,21-dione 17,17-dioxide, (7R)-14-[(1R,2S) or (1S,2R)-2-fluorocyclohexyl]-21,24-dimethyl-7,8-dihydro-6H-7,11-(epiminoethanoiminopropanothioiminomethano)indolo[1,2-e][1,5]benzoxazocin-15-one 17,17-dioxide, and pharmaceutically acceptable salts thereof.

15. A pharmaceutical composition comprising an effective amount of a compound of the formula (I), or a pharmaceutically acceptable salt thereof, according to claim 1 and a pharmaceutically acceptable carrier.

* * * * *

UNITED STATES PATENT AND TRADEMARK OFFICE
CERTIFICATE OF CORRECTION

PATENT NO. : 7,767,660 B2  
APPLICATION NO. : 12/002996  
DATED : August 3, 2010  
INVENTOR(S) : Ian Stansfield et al.

Page 1 of 1

It is certified that error appears in the above-identified patent and that said Letters Patent is hereby corrected as shown below:

On the Title Pg.

Below Item (65) Prior Publication Data, insert:

Item --(30) Foreign Application Priority Data

Dec. 20, 2006  (GB).................................0625345.4--

Signed and Sealed this
Thirty-first Day of January, 2012

David J. Kappos
*Director of the United States Patent and Trademark Office*